United States Patent [19]

Polt

[11] Patent Number: 5,981,783
[45] Date of Patent: Nov. 9, 1999

[54] CHIRAL LIGAND SYSTEM FOR MAIN GROUP AND TRANSITION METAL CATALYSTS

[75] Inventor: Robin L. Polt, Tucson, Ariz.

[73] Assignee: Polt Hill Institute, Tucson, Ariz.

[21] Appl. No.: 09/058,756

[22] Filed: Apr. 10, 1998

Related U.S. Application Data

[60] Provisional application No. 60/043,855, Apr. 11, 1997.

[51] Int. Cl.$^6$ ..................................................... C07F 15/04
[52] U.S. Cl. ................................ 556/138; 556/7; 556/110; 502/150; 502/162; 502/165; 502/167; 423/413; 540/452; 540/465
[58] Field of Search ..................................... 556/138, 110, 556/7; 502/150, 162, 167, 165; 423/413; 540/452, 465

[56] References Cited

U.S. PATENT DOCUMENTS 4,888,032  12/1989  Busch ........................................... 55/38
5,284,563  2/1994  Fugihira et al. ......................... 204/252

OTHER PUBLICATIONS

Dangle, B.D. and R.L. Polt, "Development of Micro–Metallo Enzymes for Use as Asymmetric Epoxidation Catalysts", *American Chemical Society 213th ACS National Meeting*, Abstract of Papers (1997).

Gross et al., "Remarkable Effects of Metal, Solvent, and Oxidant on Metalloporphyrin–Catalyzed Enantioselective Epoxidation of Olefins", *J. Org. Chem.* 62(16):5514–21 (1997).

Irie et al., "Catalytic Asymmetric Epoxidation of Unfunctionalized Olefins", *Tetrahedron Letters* 31(50): 7345–7348 (1990).

Koola, J. D. and J.K. Kochi, "Nickel Catalysis of Olefin Epoxidation", *Inorg. Chem.* 26:908–916 (1987).

Kinneary et al., "Alkene Epoxidation Using Ni(II) Complexes of Chiral Cyclams", *Tetrahedron Letters* 29(8): 877–880 (1988).

Mukaiyama, Teruaki, "New Possibilities in Organic Synthesis", *Aldrichimica Acta* 29(3):59 & 67–73 (1996).

Samsel et al., "Mechanism of the Chromium–Catalyzed Epoxidation of Olefins. Role of Oxochromium (V) Cations", *J. Am. Chem. Soc.* 107(25): 7606–7611 (1985).

Terekhova et al., "Equilibrium CH Acidity of Ni(II) Complexes of Schiff's Bases of Amino Acids with S–2–N–(N'–Benzylprolyl) Amino–Benzaldehyde and S–2–N–(N'–Benzylprolyl) Aminolbenzophenone", *Izv. Akad. Nauk SSR, Ser. Khim.* 4:905–909 (1986).

*Primary Examiner*—Shailendra Kumar
*Attorney, Agent, or Firm*—Quarles & Brady LLP

[57] ABSTRACT

A chiral ligand system for transition or main group metal catalysts is disclosed. These ligands can be readily synthesized using inexpensive amino acids and diamines as starting materials. Several different transition or main group metals have been inserted into the ligands. The ligands have been shown to have a tetradhedral distortion that may contribute to enhanced chiral transfer from the catalyst to the substrate in chemical modifications of olefins and other reactive substrates. These catalysts have been demonstrated to be effective in catalyzing epoxidation of a variety of substrates.

8 Claims, 2 Drawing Sheets

5,981,783

CHIRAL LIGAND SYSTEM FOR MAIN GROUP AND TRANSITION METAL CATALYSTS

CROSS-REFERENCE TO RELATED APPLICATIONS

This application claims priority to U.S. Provisional Ser. No. 60/043855, filed Apr. 11, 1997.

STATEMENT REGARDING FEDERALLY SPONSORED RESEARCH OR DEVELOPMENT

Not applicable.

BACKGROUND OF THE INVENTION

There is a great deal of interest in developing economical means for the synthesis of useful compounds by the chemical modification of relatively simple organic molecules, such as olefins (alkenes). Organic compounds that lack symmetry have two different configurational forms, or enantiomers. Frequently, a specific configuration or enantiomer may be preferred for a particular application. Chemical modifications can be conducted more efficiently when a catalyst is included. The interest in obtaining specific configurations of organic molecules by efficient means has made the development of catalysts that mediate enantioselective group transfer to relatively unfunctionalized olefins an important goal in organic chemistry.

Catalytic systems are known to the art, but these systems are unsatisfactory because the substrates must have specific functional groups to achieve the pre-coordination required for high enantioselectivity. This restriction is lifted when the stereoselectivity relies solely on non-bonded interactions. Extensive research in the enantioselective atom or group transfer to unfunctionalized olefins has led to the recent discovery of synthetically useful catalysts for a variety of chemical modifications, including for example the addition of hydroxyl groups, epoxy groups, and alkyl groups.

Ligated systems with $C_2$-symmetry have been found to be useful for asymmetric reactions and other catalytic transformations. The [14] $aneN_4$ macrocycles (cyclams) and salen based ligands have been synthesized and found to stabilize unusual geometries and oxidation states of transition or main group metals. These systems are effective in catalyzing epoxidation reactions; however, the synthesis of such ligands is generally a laborious process. This has led to an interest in the development of chiral ligands that can be easily synthesized from inexpensive chiral starting materials. In addition, there is interest in developing an epoxidation method that uses an inexpensive and environmentally safe oxygen atom source.

Chemists and enzymologists have been-studying and attempting to duplicate the high efficiency of metalloproteins for over 70 years. Of particular interest are the metalloporphyrins, which display a wide variety of chemical reactivity, principally due to their ability to complex almost any of the transition or main group metals (*Porphyrins and Metalloporphyrins*, Smith and Elsevier, Amsterdam, 1975; The *Porphyrins*, Dolphin, Academic Press, New York, 1979). Most of the metalloporphyrin chemistry has been developed in a "self-governing field" far removed from the practical constraints imposed by the requirements of catalysis and organic synthesis (Menuier, B., *Bull Soc. Chim. Fr.* 578–594, 1986). Exquisitely powerful and selective catalysts have been designed based on the porphyrin ring system (Holm, R. H., *Chem. Rev.* 87: 1401–1449, 1987), but the lengthy synthesis required to produce these metal-binding moieties may preclude their widespread use as practical chemical catalysts. Another approach that has been employed in the development of catalysts is to use a peptide backbone (Margerum, D. W., *Pure Appl. Chem.* 55: 23–34, 1983), or a peptide-derived macrocycle (Hsiao and Hegedus, *J. Org. Chem.* 62: 3586–91, 1997; Busch, D. H., *Acc. Chem, Res.* 11: 392–400, 1978) to bind metals.

What is needed in the art is a ligand system that can be readily synthesized and which is capable of catalyzing the enantioselective transfer of an atom or group to an unfunctionalized olefin.

BRIEF SUMMARY OF THE INVENTION

The present invention is a ligand system catalyst for use in the chemical modification of an olefin or other reactive substrate.

In another embodiment, this invention is a method of making a ligand system catalyst for use in the chemical modification of an olefin by inserting a transition or main group metal into a ligand.

Another aspect of this invention is a method for chemically modifying an olefin or other reactive substrate by reacting the olefin or other reactive substrate with a second substrate in the presence of the ligand system catalyst of the present invention.

It is an object of the present invention to provide an economical ligand system that can catalyze the enantioselective or regioselective transfer of an atom or group to a relatively unfunctionalized olefin or other organic substrate.

It is a further object of the present invention to provide a method of synthesizing a ligand system that is able to catalyze the enantioselective or regioselective transfer of an atom or group to an olefin by reacting a ligand with a compound comprising a transition or main group metal under suitable reaction conditions.

Another object of the present invention is to provide a method of enantioselectively or regioselectively transferring an atom or group to an olefin or other reactive substrate by reacting the substrates in the presence of an effective amount of the catalyst of the present invention.

It is a feature of the present invention that the ligand system catalyst can be synthesized using a simple synthetic scheme and relatively inexpensive precursor materials.

Other objects, features, and advantages of the present invention will be apparent from review of the specification.

DETAILED DESCRIPTION OF THE INVENTION

Figure 1:
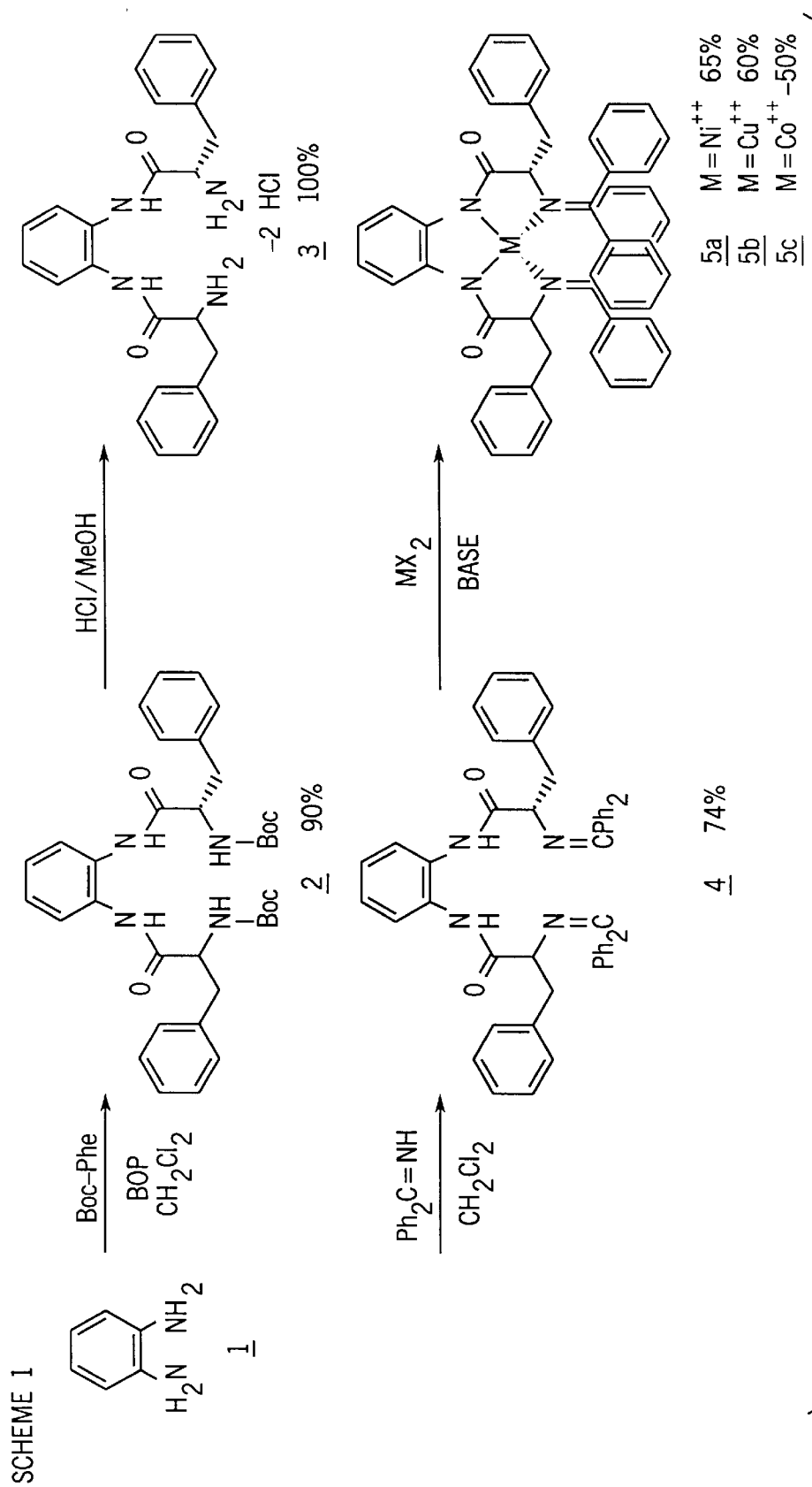
FIG. 1 is a schematic representation of the reactions used in the synthesis of chiral ligand complexes.

The present invention is a ligand system catalyst having the following structure

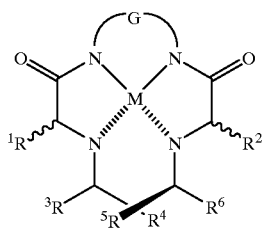

wherein R1 and R2 can be hydrogen atoms or carbon-containing moieties, most preferably having an amino acid side chain. R1 and R2 may be the same moiety or different moieties. In one embodiment, R1 and R2 are benzyl ($CH_2Ph$) groups. R3–R6 can be any organic moiety, preferably a moiety having a ring structure. R3–R6 may have the same moiety or different moieties. In the examples below, R3–R6 each comprises a phenyl group. However, it is specifically envisioned that R3–R6 can be any unsaturated, 6 member ring, preferably an aromatic ring. In another embodiment, it is reasonably anticipated that R3–R6 could be a 5 member ring, preferably having at least one double bond. G can be any molecular moiety such as a polymer substrate, boron, or an aromotic moiety, or an olefinic chain or aliphatic chain.

In the examples below, ligand transition or main group metal complexes have been formed using divalent nickel, copper, cobalt, and iron. It is reasonably expected that any transition or main group metal may be used in this invention. It is also expected that any transition or main group metal ions other than a divalent ion will be suitable in the practice of this invention.

The present invention is also a method of making a ligated metal catalytic with the possibility for enantioselective or regioselective catalysis. The first step in producing a ligand system catalyst is to provide a ligand with the following structure

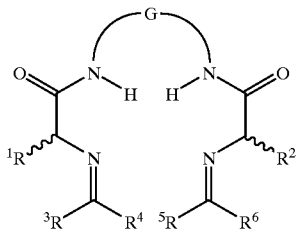

wherein R1 and R2 can be hydrogen atoms or carbon containing moieties, most preferably having an amino acid side chain. R1 and R2 may be the same moiety or different moieties. In one embodiment, R1 and R2 are benzyl ($CH_2Ph$) groups.

In the examples below, R3–R6 each comprise a phenyl group. However, it is expected that ligands having other organic moieties at R3–R6 may be effective in catalyzing a chemical modification of an olefin. The structures of ligand comprising phenyl groups at R3–R6 was determined by X-ray analysis. A key feature of these complexes is that they possess a helical axis running through the metal. This conformation is believed to be due to tetrahedral distortion caused by stacking between the $Ph_2C=N$ groups of R4 and R5. This distortion may enhance chirality transfer from the catalyst to the substrate. It is therefore expected that ligands synthesized to include organic moieties other than phenyl that are capable of stacking will be useful as catalysts. It is anticipated that R3–R6 may have the same moiety or different moieties. Preferably, the organic moiety at R3–R6 is a ring structure. It is specifically envisioned that R3–R6 can be any unsaturated, 6 member ring, preferably an aromatic ring. In another embodiment, it is reasonably anticipated that R3–R6 could be a 5 member ring, preferably having at least one double bond.

As described below, ligand system complexes have been synthesized in which G was $C_6H_4$, $C_2H_4$, $C_3H_6$, $C_3H_6$, $N=C-C=C-C=N$, and $C_{10}H_6$. It is reasonably expected that a ligand system in which G is a moiety such as boron, a polymer substrate, an aromatic moiety, or any aliphatic chain may be easily synthesized and employed in the practice of the present invention.

To make the ligand system catalyst shown and described above, a transition or main group metal ion is inserted into a ligand synthesized according to scheme 1 (FIG. 1) by reacting the ligand with a suitable compound comprising a transition or main group metal under suitable reaction conditions for a period of time sufficient to allow insertion of the metal into the ligand. Examples of suitable reactants and reaction conditions are described in detail below. However, it is expected that any method of inserting a metal ion into a ligand could be employed in the practice of this invention.

Optionally, the ligand system catalyst may be isolated from the reaction mixture as described in the examples, or using any method known to the art.

The present invention is a method for transferring an atom or a group to an olefin or other reactive substrate, comprising the step of reacting the olefin or reactive substrate with a second substrate under suitable reaction conditions in the presence of a ligand system catalyst of the present invention, the second substrate being a suitable donor for the atom or group to be transferred. The examples below describe the epoxidation of various olefins using a nickel catalyst and any of several different oxidants. Reactive substrates include compounds such as acetylenes, ketones, esters, and organic acids. It is expected that catalysts can be designed and synthesized to catalyze a variety of other chemical modifications to olefins and other reactive substrates, including for example asymmetric dihydroxylation, alkylation, oxidation, aziridination, cyclopropanation, hydrosilation, hydroxylation, and hydroboration.

The ligand system catalysts described in the Examples were designed to approximate the active site of catalytic metalloproteins. This work was undertaken with the expectation that because the active site of the typical protein catalyst comprises only a few amino acids, it would be possible to synthesize an "active site" using a simple achiral diamine that would serve to bring two optically active amino acid residues into close proximity.

The examples below describe a simple, chemically efficient synthesis of ligand systems with chirality incorporated from amino acids. A variety of transition or main group metal-binding geometries are accessible with these ligand systems. This allows for development of a variety of catalysts. The creation of new symmetry elements centered on the metal is ideal and will allow for the efficient transfer of chirality to the substrate upon catalysis. Included among the ligand systems that were synthesized are $C^2$-symmetric tetradentate complexes and nonsymmetrical complexes. In addition, other ligand systems having other geometries were synthesized by the introduction of other linkers and more functionalized amino acids capable of metal binding.

The following nonlimiting examples are intended to be purely illustrative.

EXAMPLES

Example 1

Synthesis of Chiral Ligands

The synthesis of ligand complexes 5a, 5 and 5c which include $Ni^{II}$, $Cu^{II}$, and $Co^{II}$, respectively, is shown in Scheme 1 (FIG. 1). Phenylene diamine 1a, was doubly acylated with boc-L-phenylalanine (L-Phe) with various condensation agents (DCC or BOP) to provide the Boc-protected bis-amide 2a in excellent yield. (N-Boc protection of L-Phe was achieved by reacting the chiral amino acid with Boc anhydride in a $Na_2HCO_3$ solution of dioxane and water). Following the acylation of phenylene diamine, the Boc-groups were quantitatively removed from L-Phe with HCl in methanol to yield crystalline 3a, which was treated with diphenylketimine to obtain the Schiff base 4a in 74% yield. This synthesis is described in detail in Dangel, et al. (J. Am. Chem. Soc. 119:10865-10866, 1997), which is incorporated by reference herein.

Figure 2:
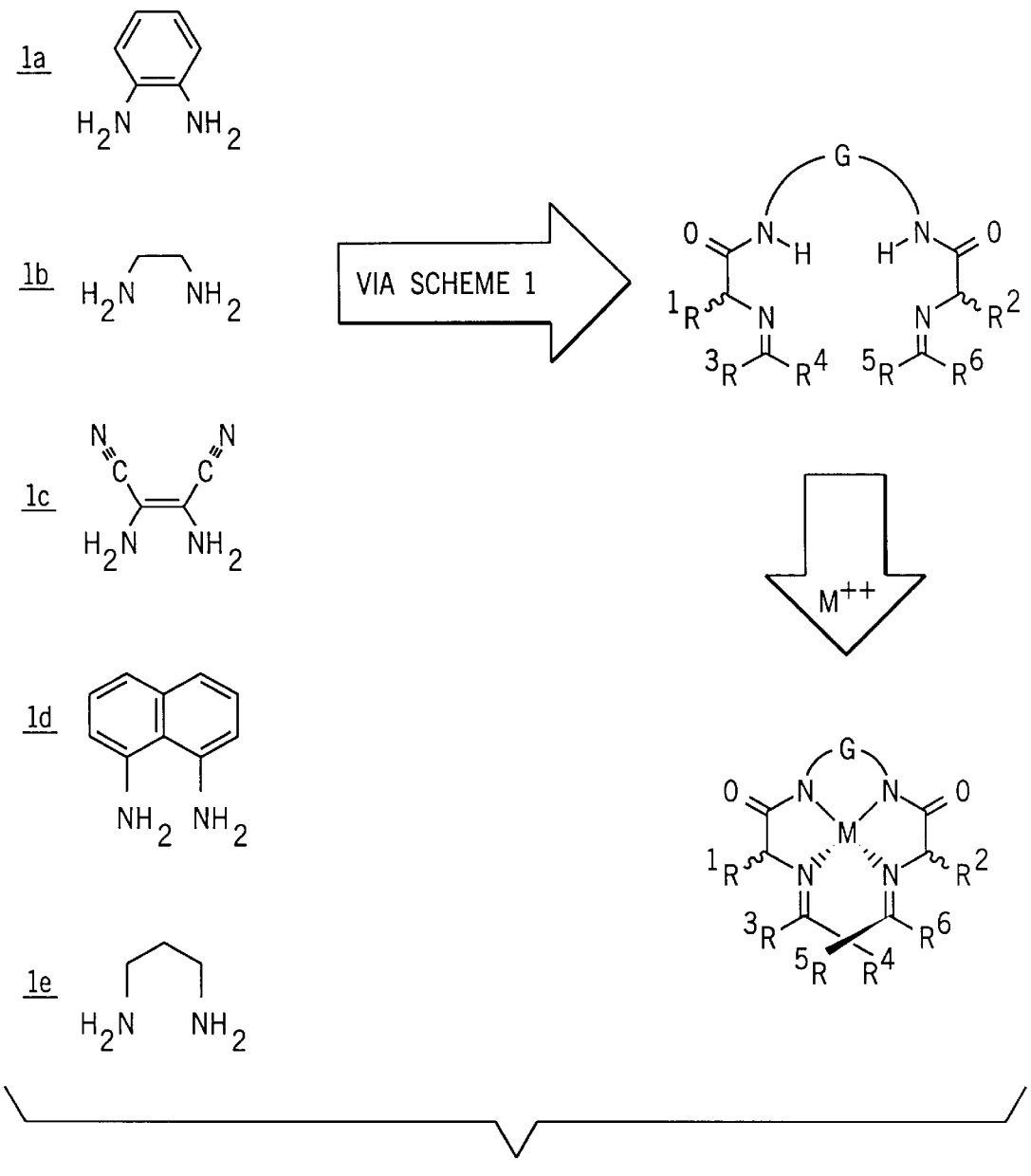
FIG. 2 shows the structures of diamines (1a–1e) that have been used in the synthesis of chiral ligand complexes.

Numerous ligands in addition to 4a were synthesized the steps shown in Scheme 1 (FIG. 1) using a variety of diamines as starting materials (Scheme 2, FIG. 2) to obtain ligands having different G groups. In addition, several different ligands were synthesized by acylating phenylene diamine using various tBoc-protected amino acids in the condensation reaction of Scheme 1 (FIG. 1). Amino acids that have been used to date in ligand synthesis include boc-protected glycine, histidine, cysteine, and serine. This has resulted in the synthesis of the following ligands: R1 and R2 are both hydrogen; R1 is a histidine side chain and R2 is; R1 and R2 are histidine side chains; R1 is a serine side chain and R2 is a benzyl moiety; R1 and R2 are both serine side chains; R1 is a cysteine side chain and R2 is a benzyl moiety; and R1 and R2 are both cysteine side chains.

Example 2

Insertion of Metal into Ligands and Characterization of the Chiral Ligand Transition or Main Group Metal Complexes.

Nickel insertion into ligand 4a was achieved by reaction with $NiBr_2$ and refluxing in methanol in the presence of $Et_3N$ for 30 hours. This reaction yielded the deep maroon, crystalline complex 5a which is air-stable, water-stable, and readily chromatographed on $SiO_2$. This low-spin complex was characterized by $^1$H-NMR, and provided crystals suitable for single-crystal X-ray analysis. Structure elucidation by X-ray crystallography revealed two rotamers per unit cell. The complex is essentially square planar with a slight tetrahedral distortion about the central axis.

A single crystal of 5a was subjected to X-ray analysis, and a preliminary structure (R=8%) was obtained. Two molecules, a totally symmetric molecule, processing a $C^2$ axis, and an unsymmetric molecule were observed in the unit cell, differing predominantly by rotation about one αC-βC bond in a phenylalanine residue. Thus, the solid-phase X-ray data strongly supported the NMR data obtained in $CdCl_3$ solution. In addition to rotation about the phenylalanine side chain, the two conformations differed in metal geometry as well (Table 1). In both molecules the Ni—N=CPh$_2$ bond lengths were somewhat longer than the Ni—N—C=O bond lengths, and the complexes are more trapezoidal, relative to porphyrin complexes, which tend to be more planar and strictly square. While the symmetric molecule showed almost no deviation from square planarity, the four nitrogens in the unsymmetric molecule showed a noticeable tetrahedral distortion (0.119 Å rms deviation overall from the ideal plane). The $Ph_2C$=N— groups were observed to be "stacked" in both cases, a factor which undoubtedly adds to the "helical twist" about the metal.

TABLE 1

| Bond lengths and angles of a chiral ligand metal catalyst | | |
|---|---|---|
| | 5a' | 5a" |
| Selected Bond Lengths | | |
| Ni—N(1) | 1.99Å | 1.98Å |
| Ni—N(2) | 1.88Å | 1.87Å |
| Ni—N(3) | 1.87Å | 1.83Å |
| Ni—N(4) | 1.98Å | 1.93Å |
| Selected Bond Angles | | |
| N(1)-Ni—N(2) | 81.5° | 85.0° |
| N(2)-Ni—N(3) | 85.6° | 83.2° |
| N(3)-Ni—N(4) | 82.5° | 82.0° |
| N(1)-Ni—N(4) | 110.4° | 110.7° |
| rms dev from plane | 0.020Å | 0.119Å |

Copper metal was inserted into the ligand of 4a by reacting the ligand with $CuCl_2$ in DMF at room temperature in the presence of DBU. The reaction produced complex 5b, which was purified by flash chromatography and recrystallization to obtain brown crystals. The complex 5b was subjected to electron spin resonance spectroscopy at 9.447 Ghz. the brown cyrstals of 5b after flash chromatography on $SiO_2$. This paramagnetic complex was subjected to EPR analysis. The EPR parameters were evaluated from a combination of glass and liquid state spectra. Simulation of the spectra based on QPWA is in progress. From preliminary data we can conclude that the complex is qualitatively similar to $Cu^{II}$ tetraphenylporphyrin complexes, but with increased tetrahedral distortion from square planarity. This distortion can also be described as a screw axis centered on the metal. Strong evidence for the helical nature of these complexes was provided by the unusually large optical rotation upon insertion of the metal.

Complex 5c was produced in $CH_3CN$ with $CoCl_2$ and $NaN(SiME_3)_2$ as a base. The high spin tetracoordinate CoI complex proved to be unstable on $SiO_2$, and was isolated by recrystallization from $CH_3CN$/hexanes or $CH_2Cl_2$/hexanes to yield deep blue crystals. The paramagnetic complexes were subjected to e.p.r. analysis.

Iron was also inserted into the ligand by reacting $FeCl_3$ and acetonitrile at room temperature for several hours.

Example 3

Epoxidation of Olefins

The epoxidation of simple cis- and trans-olefins was examined using complex 5a and commercial bleach (NaOCl) as an oxidant. No attempt was made to optimize the reactions. The trans-epoxides were observed as the major product in every case, regardless of the starting olefin geometry. While the e.e.'s were not large (~4%), turnover numbers of 12–14 were observed with trans-β-methylstyrene and 5a, indicating that the ligand system can function under the conditions of catalysis.

Epoxidation studies have been done on several olefins using the nickel catalyst. Three oxidants (iodosyl benzene, sodium hypochlorite and Oxone®) have been examined as the oxygen atom source. A general procedure for each case study is provided below.

In a glass vial commercial bleach (5.25% NaOCL; 6.6 ml) and 0.05 M Na$_2$HPO$_4$ (2.5 ml) were combined and the pH was adjusted to 11 with 1 N NaOH. The solution was cooled to 0° C. In a separate 50 ml glass round bottom the Ni catalyst (67.7 mg; 0.08 mol., 4 mol %), nBu$_4$NBr (30 mg; 0.09 mol., 4 mol %) and trans-beta-methyl styrene were combined with the chilled buffered bleach solution and the two phases were agitated for 5 hours at room temperature. The original brown mixture began to precipitate a black solid after a few hours of reaction time. Aqueous bicarbonate work-up followed by column chromatography gave the trans epoxide in 37% yield. Attempts to examine the optical activity by $^1$H NMR in the presence of Eu(hfc)$_3$ showed no asymmetric induction.

In the iodosyl benzene case, the olefin, Ni catalyst, and oxidant were combined and slurried in acetonitrile for 24 hours. A small amount of epoxide was formed and observed by $^1$H NMR.

Using Oxone® as the oxidant under similar conditions as the hypochlorite showed almost no formation of the epoxide. Changing the phase transfer catalyst from nBu$_4$NBr to benzyltriethyl ammonium chloride showed the formation of the epoxide in approximately a 10–15% conversion by NMR.

A summary of the epoxidation results is provided in Table 2. The epoxidation conditions remained constant throughout the studies. All reactions using sodium hypochlorite and Oxone® were bi-phasic and the concentration of the aqueous phase was approximately 0.5 M in oxidant. The % epoxide formed was determined by calculating the ratio of the NMR peak areas (epoxide to starting olefin). Note that in the absence of the nickel catalyst there was some formation of the epoxide.

The tetrahedral distortion observed with the complexes that have been synthesized and characterized may provide an important degree of chirality transfer in addition to the chiral stearic environment provided by the chiral ligands (R groups). It is expected that the ligands may also accommodate alkyl, carbene, pi-olefin and pi-acetylene complexes by substituting various metals, thereby allowing catalysis of reactions in addition to the epoxidation reactions.

TABLE 2

Epoxidation results using the nickel catalyst, various oxidants and phase transfer catalysts

| Mole % Ni | Phase transfer catalyst | Oxidant | Molarity | Substrate | Product | % Epoxide |
| --- | --- | --- | --- | --- | --- | --- |
| 22 | — | PhI=O | — | cis-stilbene | trans-oxide | <5 |
| 16 | — | PhI=O | — | trans-stilbene | trans-oxide | <5 |
| 4 | nBu$_4$NBr (4 mol %) | NaOCl | 0.62M | trans-β-methyl styrene | trans-oxide | 58 |
| 4.8 | nBu$_4$NBr (4 mol %) | NaOCl | 0.46M | trans-stilbene | trans-oxide | 37 |
| 4 | nBu$_4$NBr (4 mol %) | NaOCl | 0.46M | cis-stilbene | trans-oxide cis-oxide | 15 |
| 5.1 | nBu$_4$NBr (4 mol %) | NaOCl | 0.54M | styrene | styrene-oxide | <1 |
| 4.5 | nBu$_4$NBr (4 mol %) | NaOCl | 0.46M | Indene | Indene-oxide | <5 |
| 1.3 | Benzyltriethyl ammonium chloride (6.5 mol %) | Oxone® | 0.048M | trans-stilbene | trans-oxide | 10 |
| 1.3 | Benzyltriethyl ammonium chloride (5.8 mol %) | Oxone® | 0.048M | cis-stilbene | trans-oxide cis-oxide | <1 |
| 4 | nBu$_4$NBr (4 mol %) | Oxone® | 0.48M | cis-stilbene | trans-oxide | 1 |
| 4 | nBu$_4$NBr (4 mol %) | Oxone® | 0.48M | cis-stilbene | trans-oxide | 1 |
| 0 | nBu$_4$NBr (4 mol %) | NaOCl | 0.54M | trans-β-methyl styrene | trans-oxide | 14 |
| 0 | — | NaOCl | 0.50M | trans-β-methyl styrene | trans-oxide | 7 |

It is claimed:

1. A ligand system catalyst comprising the structure

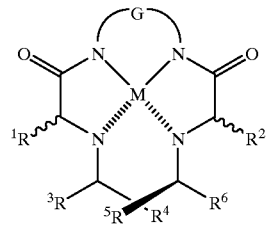

wherein R1 is selected from the group consisting of H and an organic moiety, wherein R2 is selected from the group consisting of H and an organic moiety, wherein R3, R4, R5, and R6 are selected from the group consisting of an unsaturated, organic 5 member ring and an unsaturated, organic 6 member ring, wherein M is selected from a group consisting of the transition or main group metals, and wherein G is selected from a group consisting of boron, a polymer substrate, an aromatic moiety, an olefinic moiety, and an aliphatic moiety.

2. The catalyst of claim 1, wherein G is selected from the group consisting of C$_6$H$_4$, C$_2$H$_4$, C$_3$H$_6$, C$_3$H$_6$,N=C—C=C—C=N, and C$_{10}$H$_6$.

3. The catalyst of claim 1, wherein R3, R4, R5, and R6 are phenyl groups.

4. The catalyst of claim 1, wherein R1 is selected from the group consisting of H, benzyl, a histidine side chain, a serine side chain, and a cystine side chain, and wherein R2 is selected from the group consisting of H, benzyl, a histidine side chain, a serine side chain, and a cysteine side chain.

5. A method for making a ligand system catalyst comprising the steps of:

(a) providing a ligand having the following structure

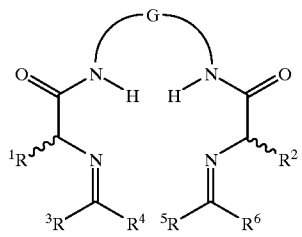

wherein R1 is selected from a group consisting of H and an organic moiety, wherein R2 is selected from a group consisting of H and an organic moiety, wherein R3, R4, R5, and R6 are selected from a group consisting of an unsaturated, organic 5 member ring and an unsaturated, organic 6 member ring, wherein X is selected from a group consisting of the transition or main group metals, and wherein G is selected from a group consisting of boron, a polymer substrate, an aromatic moiety, an olefinic moiety, and an aliphatic moiety; and (b) reacting the ligand of step (a) with a suitable compound comprising a metal selected from a group consisting of the transition or main group metals under suitable reaction conditions for a period of time sufficient to allow insertion of the metal into the ligand.

6. The method of claim 5, wherein G is selected from the group consisting of $C_6H_4$, $C_2H_4$, $C_3H_6$, $C_3H_6$,N=C—C=C—C=N, and $C_{10}H_6$.

7. The method of claim 5, wherein R3, R4, R5, and R6 are phenyl groups.

8. The method of claim 5, wherein R1 is selected from the group consisting of H, benzyl, a histidine side chain, a serine side chain, and a cystine side chain, and wherein R2 is selected from the group consisting of H, benzyl, a histidine side chain, a serine side chain, and a cysteine side chain.

* * * * *